United States Patent
Shalaby

(10) Patent No.: US 7,048,753 B2
(45) Date of Patent: May 23, 2006

(54) COATED, SLOW-ABSORBING TEXTILE CONSTRUCTS FOR SUTURES AND TISSUE ENGINEERING

(75) Inventor: Shalaby W. Shalaby, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 938 days.

(21) Appl. No.: 10/086,312

(22) Filed: Mar. 1, 2002

(65) Prior Publication Data

US 2002/0120291 A1    Aug. 29, 2002

Related U.S. Application Data

(63) Continuation-in-part of application No. 09/862,093, filed on May 21, 2001, which is a continuation of application No. 09/523,754, filed on Mar. 13, 2000, now Pat. No. 6,342,065.

(60) Provisional application No. 60/124,838, filed on Mar. 17, 1999.

(51) Int. Cl.
*A61B 17/04*    (2006.01)

(52) U.S. Cl. ................ 606/230; 606/231; 525/415; 528/354

(58) Field of Classification Search ........... 606/230, 606/231, 228; 528/354, 357; 424/426; 525/415
See application file for complete search history.

(56) References Cited

U.S. PATENT DOCUMENTS

| 6,342,065 | B1* | 1/2002 | Shalaby | 606/230 |
| 6,703,035 | B1* | 3/2004 | Shalaby | 424/408 |
| 2002/0155159 | A1* | 10/2002 | Shalaby | 424/486 |
| 2004/0161465 | A1* | 8/2004 | Shalaby | 424/486 |

* cited by examiner

*Primary Examiner*—Henry Bennett
*Assistant Examiner*—Dinnatia Doster-Greene
(74) *Attorney, Agent, or Firm*—Leigh P. Gregory

(57) ABSTRACT

The present invention is directed to crystalline copolymers of l-lactide and a minor portion of a cyclic monomer, preferably ε-caprolactone or trimethylene carbonate or both. The present copolymers have a melting temperature of at least 150° C. and a crystallinity of at least 20%. Preferred are high molecular weight copolymers having an inherent viscosity of at least 1.1 dl/g. A variety of surgical constructs may be formed from the present copolymers. Disclosed are coated surgical constructs including sutures made of multifilament yarns of the present copolymers and coated with nitrogenous copolyesters which will bioabsorb in less than three years and will maintain at least 50% of their initial strength three weeks post-operatively.

8 Claims, No Drawings

COATED, SLOW-ABSORBING TEXTILE CONSTRUCTS FOR SUTURES AND TISSUE ENGINEERING

The present application is a continuation-in-part of U.S. Ser. No. 09/862,093, filed May 21, 2001, which is a continuation-in-part of U.S. Ser. No. 09/523,754, filed Mar. 13, 2000, which issued as U.S. Pat. No. 6,342,065 and which claims benefit of provisional U.S. Ser. No. 60/124,838, filed Mar. 17, 1999.

BACKGROUND TO THE INVENTION

It is well established in the prior art that absorbable fibers suitable for constructing biomedical constructs with prolonged strength retention profile, as in certain surgical sutures and meshes as well as prosthetic tendons and ligaments, need to be based on polymers having (1) high molecular weight; (2) a high degree of crystallinity; and (3) minimum or no monomeric species. These requirements were claimed to have been fulfilled by the l-lactide/glycolide copolymers described in U.S. Pat. No. 5,425,984 and EP Application No. 241,252 (1987). However, in certain high load-bearing applications where a prosthetic fibrous construct experiences cyclic stresses and is expected to maintain a substantial fraction of its initial strength for several weeks post-operatively, additional requirements are imposed. Typical examples of such constructs are surgical meshes for hernia repair and prosthetic tendons and ligaments. These additional requirements are expected to be associated with having a high degree of toughness, as measured in terms of the work required to break, without compromising, significantly, their high tensile strength, high elastic modulus, low stretchability, and high yield strength. Such requirements also are expected to be associated with a polymeric chain with higher hydrolytic stability than those containing glycolate sequences are. Unfortunately, the prior art of absorbable polymers provides conflicting teachings that may be applied towards meeting the aforementioned additional requirements. To increase toughness, the introduction of more flexible $\epsilon$-caprolactone-based sequences in polyglycolide chain has been used successfully in the production of low modulus sutures (see, for example, U.S. Pat. Nos. 4,605,730 and 4,700,704) but with compromised strength. A similar situation is encountered in the copolymer of glycolide and trimethylene carbonate (see, for example, U.S. Pat. No. 4,429,980). Interestingly, fibers made of these two types of copolymers do display a lower propensity to hydrolysis than polyglycolide, but their strength loss profiles remain unsuitable for long-term, load-bearing applications.

Substantial developments in the field of tissue engineering were made possible by the availability of absorbable polymers and their use as a scaffold for cell attachment and growth in three-dimensions. However, almost all of the applications of absorbable polymers in tissue engineering were based on polyglycolide or high glycolide copolymers, which lose their mechanical integrity within four weeks. Meanwhile, the new trends in tissue engineering research rely on implanting the absorbable scaffold at biological sites that require the retention of their mechanical integrity well over a period of four weeks. Such contemporary requirements and consistent call for substrates that encourage cell attachment as well as being biomechanically compatible with active cells provided an incentive to explore the feasibility of designing absorbable chain molecules with the aforementioned requirements and other desirable features for their use in tissue engineering applications. And this invention deals with the synthesis of segmented, high lactide, absorbable copolymers which can be easily converted to textile constructs for use as scaffolds for tissue ingrowth having (1) a strength retention profile that allows the retention of their mechanical properties well beyond the four-week limit of presently used synthetic absorbables; (2) an absorbable surface coating that is compliant and carries a positive charge which encourages cell attachment; and (3) a discernable fraction of very low $T_g$, compliant segments that dominate the fiber surface and hence, provide a biomechanically compatible substrate for actively growing cells.

SUMMARY OF THE INVENTION

The present invention is directed to a bioabsorbable textile construct which includes a preliminary article made of a crystalline copolymer which is a copolymer of l-lactide and at least one cyclic monomer, wherein the cyclic monomer is a liquid at or above about 40° C., wherein the l-lactide derived sequences of the polymer chain are crystallizable segments or blocks and comprise from about 60 to about 99 percent of all sequences, and wherein the copolymer has a $T_m$ of at least 150° C., exhibits a crystallinity of at least about 20%, and has an inherent viscosity of at least about 1.0 dl/g; and a coating of a nitrogenous copolyester having a molecular weight of less than 20,000 Da which includes chain sequences covalently linked to a central nitrogen of a tertiary amine, the chain sequences comprising from about 90 to about 98 percent by mole of caprolactone-based units and from about 2 to about 10 percent by mole of glycolide-based units.

Additionally, the present invention is directed to a bioabsorbable textile construct which includes a preliminary article made of a crystalline copolymer which is a copolymer of l-lactide and at least one cyclic monomer, wherein the cyclic monomer is a liquid at or above about 40° C., wherein the l-lactide derived sequences of the polymer chain are crystallizable segments or blocks and comprise from about 60 to about 99 percent of all sequences, and wherein the copolymer has a $T_m$ of at least 150° C., exhibits a crystallinity of at least about 20%, and has an inherent viscosity of at least about 1.0 dl/g; and a coating of a nitrogenous copolyester having a molecular weight of less than 20,000 Da which includes chain sequences having a major portion of units derived from cyclic monomers and a minor portion of units derived from an acid initiator, the cyclic monomer-based units comprising from about 90 to about 98 percent by mole of caprolactone-based units and from about 2 to about 10 percent by mole of glycolide-based units, wherein the acid-based units are bound to a basic amino acid.

DETAILED DESCRIPTION OF PREFERRED EMBODIMENTS

The present invention is directed to high molecular weight copolymers of a major portion of l-lactide and a minor portion of $\epsilon$-caprolactone (CL) or trimethylene carbonate (TMC) or both. High molecular weight is defined as displaying an inherent viscosity of at least 1.0 dl/g. The molar ratio of l-lactide to comonomer is between from about 60 to about 40% and from about 99 to about 1%. Preferably, the ratio is between from about 65 to about 35% and from about 95 to about 5%. More preferably, the ratio is between from about 75 to about 25% and from about 90 to about 10%. Most preferably the ratio is between from about 80 to about 20% and from about 85 to about 15%. The present copolymers, particularly the l-lactide/caprolactone copolymers of the present invention, have a degree of crystallinity of greater than about 20%.

The present invention is also directed to l-lactide/caprolactone, l-lactide/trimethylene carbonate and l-lactide/caprolactone/trimethylene carbonate-based monofilament yarn having a Young's modulus of more than 400,000 psi, a tensile strength exceeding 40,000 psi, a percent elongation of less than 50%, a $T_m$ of greater than about 150° C., and a degree of crystallinity exceeding 25%.

The present invention is also directed to l-lactide/ε-caprolactone, l-lactide/trimethylene carbonate, and l-lactide/ε-caprolactone/trimethylene carbonate-based monofilament yarn having a Young's modulus of more than 100,000 psi, a percent elongation of less than 80%, a $T_m$ of greater than 150° C., and degree of crystallinity exceeding 20%.

The present invention is also directed to l-lactide/ε-caprolactone, l-lactide/trimethylene carbonate, and l-lactide/ε-caprolactone/trimethylene carbonate-based monofilament yarn having l-lactide-based units constituting about 60 to 99% of the total chain repeat units and present in crystallizable segments or blocks.

The present invention is also directed to l-lactide/ε-caprolactone, l-lactide/trimethylene carbonate, and l-lactide/ε-caprolactone/trimethylene carbonate-based monofilament yarn having l-lactide-based units constituting about 95% of the total chain repeat units and linked at random with ε-caprolactone and/or trimethylene carbonate-based units.

The present invention is also directed to multifilament yarn having a tenacity in excess of 3 g/d with single fiber diameter of less than 35μ. In accordance with the present invention, surgical suture made of such monofilament and multifilament yarns absorb in less than 3 years and maintain at least 50% of their initial strength at three weeks post-operatively, preferably at six weeks post-operatively. Also within the scope of the present invention are prosthetic ligaments, tendons, meshes for tissue repair, and vascular grafts made totally of such multifilament yarns or a combination the present multifilaments and monofilaments or a combination with other more absorbable multifilament or monofilament yarns.

The present invention is also directed to multifilament yarn having a tenacity in excess of 2 g/d with single fiber diameter of less than 40μ. In accordance with the present invention, surgical suture made of such monofilament and multifilament yarns absorb in less than 3 years and maintain at least 50% of their initial strength at four weeks post-operatively, preferably at four weeks post-operatively. Also within the scope of the present invention are prosthetic ligaments, tendons, meshes for tissue repair, and vascular grafts made totally of such multifilament yarns or a combination the present multifilaments and monofilaments or a combination with other more absorbable multifilament or monofilament yarns.

More broadly, this invention is directed to absorbable fibers made from segmented copolymers where more than 50 percent of the mass comprises crystallizable polylactide segments and the balance is low $T_g$, soft segments. Preferably, the soft segment of the segmented copolymer is derived, primarily, from trimethylene carbonate (TMC), a mixture of ε-caprolactone and TMC, 1,5-dioxepan-2-one, a mixture of 1,5-dioxepan-2-one and ε-caprolactone, or a mixture of p-dioxanone and TMC. Such fibers may be assembled into textile constructs that can be used as scaffolds for tissue engineering in the form of knitted or woven meshes, three-dimensional woven fabrics, double knits, and non-woven fabrics, which are capable of maintaining their mechanical integrity in the biological environment or relevant in vitro media for more than four weeks and preferably more than twelve weeks. More specifically, such slow-absorbing fibers or multifilament yarn may be assembled in a twisted or braided form for use in orthopedic applications such as for use in conjunction with the repair/regeneration of tendons and ligaments and for use as sutures (or similar constructs) for reattaching soft tissue to bones. In a preferred embodiment the present invention is directed to coating such textile constructs with an absorbable nitrogenous copolyester that improves surface lubricity and provides sufficient positive charge on the surface to aid cell attachment. Preferably, the present coating composition comprises an absorbable copolymer of an ε-caprolactone and glycolide wherein the (1) copolymer is made using triethanolamine as the initiator; (2) copolymer is made using malic, citric, or tartaric acid as the initiator and the acid groups of said copolymer are partially neutralized with or covalently linked to a basic amino acid such as lysine or arginine; and (3) copolymer has a Tm of less than 60° C.

Thus, the copolymers of this invention are preferably converted to strong, yet compliant, monofilaments for use as sutures for repairing slow healing tissues, or woven and knitted meshes for repairing abdominal walls (e.g., hernial repair) or vascular walls.

Another aspect of this invention deals with a braided suture, coated with a nitrogenous copolyester coating, sterilized by ethylene oxide or other sterilization method for use in general surgery and preferably in indications requiring suture strength retention over a period of at least four weeks and preferably more than six weeks and more preferably more than twelve weeks for use in orthopedic procedures entailing sutures (or similar constructs) for reattaching soft tissue to bone. Another aspect of this invention deals with a knitted or woven mesh that may be coated with a nitrogenous copolyester for use in a tissue engineered patch for repairing vascular or abdominal walls or used in supporting the healing of said walls. Another aspect of this invention deals with a textile construct that may be coated with a nitrogenous copolyester for use in a tissue-engineered tendon, ligament or vascular graft.

Additional aspects of this invention are further illustrated by the specific examples described below.

EXAMPLE 1

Preparation of 50/50 ε-Caprolactone/Trimethylene Carbonate Initiated by 1,3-Propanediol The reaction apparatus was comprised of a 3-neck 500 ml boiling flask equipped with a penny-head stopper, a magnetic stir bar, and two 90° connectors. After obtaining a vacuum of 0.05 mmHg, the apparatus was flame dried under argon purge. An initial charge of 122.9 grams (1.204 moles) of trimethylene carbonate was added to the flask.

The apparatus and its contents were placed under room temperature vacuum for 1 hour and 15 minutes. The system was then purged with argon. Using a high temperature oil bath, the apparatus and its contents were heated to 100° C. Upon complete melting of the trimethylene carbonate, the additional charge of 137.5 grams (1.204 moles) ε-caprolactone, 1.3 grams ($1.605 \times 10^{-2}$ moles) of 1,3-propanediol, and 1.72 milliliters ($3.44 \times 10^{-4}$ moles) of a 0.2M solution of stannous octoate catalyst in toluene was added to the kettle while stirring. The temperature was then increased to 180° C. Reaction was maintained at 180° C. for 1.5 hours.

The molecular weights were determined by GPC using Dichloromethane as solvent. The results were as follows: Mn=31.6 kiloDaltons, Mw=58.9 kiloDaltons, and Mp=70.0 kiloDaltons.

EXAMPLE 2

Preparation of 80/20 ε-Caprolactone/Trimethylene Carbonate Initiated by 1,3-Propanediol The reaction apparatus was comprised of a 3-neck 500 ml boiling flask equipped with a penny-head stopper, a magnetic stir bar, and two 90° connectors. After obtaining a vacuum of 0.15 mmHg, the apparatus was flame dried under argon purge. An initial charge of 55.2 grams (0.538 moles) of trimethylene carbonate was added to the flask.

The apparatus and its contents were placed under room temperature vacuum for 1 hour. The system was then purged with argon. Using a high temperature oil bath, the apparatus and its contents were heated to 100° C. Upon complete melting of the trimethylene carbonate, the additional charge of 245.3 grams (2.15 moles) ε-caprolactone, 1.3 milliliters ($1.792 \times 10^{-2}$ moles) of 1,3-propanediol, and 1.92 milliliters ($3.84 \times 10^{-4}$ moles) of a 0.2M solution of stannous octoate catalyst in toluene was added to the flask while stirring. The temperature was then increased to 180° C. Reaction was maintained at 180° C. for 1 hour.

The molecular weights were determined by GPC using Dichloromethane as solvent. The results were as follows: Mn=45.8 kiloDaltons and Mw=76.1 kiloDaltons.

EXAMPLE 3

Preparation of Poly-ε-Caprolactone Initiated by 1,3-Propanediol

The reaction apparatus was comprised of a 1-neck 500 ml boiling flask equipped with a 90° connector and a magnetic stir bar. The apparatus was flame dried under nitrogen. An initial charge of 400.1 grams (3.509 moles) of ε-caprolactone, 1.69 milliliters ($2.339 \times 10^{-2}$ moles) 1,3-propanediol, and 2.51 milliliters ($5.01 \times 10^{-2}$ moles) of a 0.2M solution of stannous octoate catalyst in toluene was added to the flask.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature was then increased to 160° C. Reaction was maintained at 160° C. for 1.5 hours.

The molecular weights were determined by GPC using Dichloromethane as solvent. The results were as follows: Mn=31.5 kiloDaltons and Mw=47.6 kiloDaltons.

EXAMPLE 4

Preparation of Poly-Trimethylene Carbonate Initiated by 1,3-Propanediol

The reaction apparatus was comprised of a 1-neck 250 ml boiling flask equipped with a 90° connector and a magnetic stir bar. The apparatus was flame dried under nitrogen. An initial charge of 200.2 grams (1.96 moles) of trimethylene carbonate, 0.943 milliliters ($1.307 \times 10^{-2}$ moles) 1,3-propanediol, and 1.4 milliliters ($2.8 \times 10^{-4}$ moles) of a 0.2M solution of stannous octoate catalyst in toluene was added to the flask.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature was then increased to 160° C. Reaction was maintained at 160° C. for 1 hour.

The molecular weights were determined by GPC using Dichloromethane as solvent. The results were as follows: Mn=32.4 kiloDaltons and Mw=57.4 kiloDaltons.

EXAMPLE 5

Preparation of 20/80 (50/50 ε-Caprolactone/Trimethylene Carbonate)/l-Lactide Segmented Copolymer The reaction apparatus was comprised of a 1L stainless steel kettle with a 3-neck glass lid equipped with an overhead mechanical stirring unit, vacuum adapter, and two 90° connectors for an argon inlet. After obtaining a vacuum of 0.3 mmHg, the apparatus was flame dried. An initial charge of 47.5 grams (0.438 moles) 50/50 ε-caprolactone/trimethylene carbonate from example 1 and 253 grams (1.754 moles) l-lactide was added to the kettle.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature of the oil bath was increased to 140° C. and stirring initiated at 120 rpm. Upon complete melting of the contents after 30 minutes, the temperature of the oil bath was lowered to 110° C. After the 30 minutes at 110° C., 0.235 ml ($4.693 \times 10^{-5}$ moles) of a 0.2M solution of stannous octoate catalyst in toluene was added to the kettle while stirring. The temperature was then increased to 140° C., and the stir rate was decreased to 50 RPM. Stirring was stopped after 1 hour and 10 minutes. The reaction was maintained at 140° C. for 26.5 hours.

The inherent viscosity using chloroform as a solvent was 1.4 dl/g. The melting temperature and heat of fusion, as determined by differential scanning calorimetry, were 187.6° C. and 50.1 J/g, respectively.

EXAMPLE 6

Preparation of 20/80 (50/50 ε-Caprolactone/Trimethylene Carbonate)/(92/8 l-Lactide/ε-Caprolactone) Segmented Copolymer The reaction apparatus was comprised of a 1L stainless steel kettle with a 3-neck glass lid equipped with an overhead mechanical stirring unit, vacuum adapter, and two 90° C. for an argon inlet. After obtaining a vacuum of 0.4 mmHg, the apparatus was flame dried. An initial charge of 48.0 grams (0.444 moles) of 50/50 ε-Caprolactone/Trimethylene Carbonate from Example 1, 13 grams (0.111 moles) of ε-Caprolactone, and 240.1 grams (1.665 moles) of l-lactide was added to the kettle.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature of the oil bath was increased to 140° C. and stirring initiated at 120 rpm. Upon complete melting and mixing of the contents after approximately 15 minutes, the temperature was decreased to 110° C. After 30 minutes 0.238 milliliters ($4.76 \times 10^{-5}$ moles) of a 0.2M solution of stannous octoate catalyst in toluene was added to the kettle while stirring. The temperature was then increased to 140° C. and stir rate was lowered to approximately 50 rpm. Stirring was stopped after approximately 2.5 hours. The reaction was maintained at 140° C. for 26.5 hours.

The inherent viscosity using chloroform as a solvent was 1.25 dl/g. The melting temperature and heat of fusion, as determined by differential scanning calorimetry, were 175.2° C. and 59.5 J/g, respectively.

EXAMPLE 7

Preparation of 10/90 (80/20 ε-Caprolactone/Trimethylene Carbonate)/(92/8 l-Lactide/ε-Caprolactone) Segmented Copolymer The reaction apparatus was comprised of a 1L stainless steel kettle with a 3-neck glass lid equipped with an overhead mechanical stirring unit, vacuum adapter, and two 90° C. for an argon inlet. After obtaining a vacuum of 0.35 mmHg, the apparatus was flame dried. An initial charge of 25.1 grams (0.216 moles) of 80/20 ε-caprolactone/trimethylene carbonate from Example 2, 18.3 grams (0.156 moles) of ε-caprolactone, and 258.6 grams (1.793 moles) of l-lactide was added to the kettle.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature of the oil bath was increased to 140° C. and stirring initiated at 120 rpm. Upon complete melting and mixing of the contents after 5 minutes, the temperature was decreased to 110° C. After 30 minutes 0.385 milliliters ($7.71 \times 10^{-5}$ moles) of a 0.2M solution of stannous octoate catalyst in toluene was added to the kettle while stirring. The temperature was then increased to 140° C. and stir rate was lowered to approximately 40 rpm. Stirring was stopped after approximately 2 hours. The reaction was maintained at 140° C. for 26.5 hours.

The inherent viscosity using chloroform as a solvent was 2.46 dl/g. The melting temperature and heat of fusion, as determined by differential scanning calorimetry, were 176.2° C. and 42.7 J/g, respectively.

EXAMPLE 8

Preparation of 30/70 (80/20 ε-Caprolactone/Trimethylene Carbonate)/(92/8 l-Lactide/ε-Caprolactone) Segmented Copolymer The reaction apparatus was comprised of a 1L stainless steel kettle with a 3-neck glass lid equipped with an overhead mechanical stirring unit, vacuum adapter, and two 90° C. for an argon inlet. After obtaining a vacuum of 0.35 mmHg, the apparatus was flame dried. An initial charge of 75.6 grams (0.6787 moles) of 80/20 ε-caprolactone/trimethylene carbonate from Example 2, 14.6 grams (0.1267 moles) of ε-caprolactone, and 210.1 grams (1.457 moles) of l-lactide was added to the kettle.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature of the oil bath was increased to 140° C. and stirring initiated at 120 rpm. Upon complete melting and mixing of the contents after 5 minutes, the temperature was decreased to 110° C. After 30 minutes 0.081 milliliters ($1.62 \times 10^{-5}$ moles) of a 0.2M solution of stannous octoate catalyst in toluene was added to the kettle while stirring. The temperature was then increased to 140° C. and stir rate was lowered to approximately 40 rpm. Stirring was stopped after approximately 40 minutes. The reaction was maintained at 140° C. for 26.5 hours.

The inherent viscosity using chloroform as a solvent was 1.2 dl/g. The melting temperature and heat of fusion, as determined by differential scanning calorimetry, were 169.3° C. and 43 J/g, respectively.

EXAMPLE 9

Preparation of 10/90 Poly-ε-Caprolactone/(95/5 l-Lactide/Trimethylene Carbonate) Segmented Copolymer The reaction apparatus was comprised of a 1L stainless steel kettle with a 3-neck glass lid equipped with an overhead mechanical stirring unit, vacuum adapter, and two 90° connectors for an argon inlet. After obtaining a vacuum of 0.5 mmHg, the apparatus was flame dried. An initial charge of 24.8 grams (0.2157 moles) of poly-ε-caprolactone from Example 3, 10.1 grams (0.0971 moles) of trimethylene carbonate, and 265.8 grams (1.8442 moles) of l-lactide was added to the kettle.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature of the oil bath was increased to 140° C. and stirring initiated at 100 rpm. Upon complete melting and mixing of the contents after 10 minutes, the temperature was decreased to 110° C. After 30 minutes 0.385 milliliters ($7.705 \times 10^{-5}$ moles) of a 0.2M solution of stannous octoate catalyst in toluene was added to the kettle while stirring. The temperature was then increased to 140° C. and stir rate was lowered to approximately 40 rpm. Stirring was stopped after approximately 2.5 hours. The reaction was maintained at 140° C. for 26.5 hours.

The inherent viscosity using chloroform as a solvent was 2.16 dl/g. The melting temperature and heat of fusion, as determined by differential scanning calorimetry, were 176.8° C. and 54 J/g, respectively.

EXAMPLE 10

Preparation of 10/90 Trimethylene Carbonate/(95/5 l-Lactide/Trimethylene Carbonate) Segmented Copolymer The reaction apparatus was comprised of a 1L stainless steel kettle with a 3-neck glass lid equipped with an overhead mechanical stirring unit, vacuum adapter, and two 90° C. for an argon inlet. After obtaining a vacuum of 0.35 mmHg, the apparatus was flame dried. An initial charge of 22.2 grams (0.2175 moles) of poly-trimethylene carbonate from example 4, 10 grams (0.0979 moles) of trimethylene carbonate, and 267.9 grams (1.8596 moles) of l-lactide was added to the kettle.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature of the oil bath was increased to 140° C. and stirring initiated at 120 rpm. Upon complete melting and mixing of the contents after 25 minutes, the temperature was decreased to 110° C. After 30 minutes 0.389 milliliters ($7.768 \times 10^{-5}$ moles) of a 0.2M solution of stannous octoate catalyst in toluene was added to the kettle while stirring. The temperature was then increased to 140° C. and stir rate was lowered to approximately 40 rpm. Stirring was stopped after approximately 1 hour. The reaction was maintained at 140° C. for 26.5 hours.

The inherent viscosity using chloroform as a solvent was 2.85 dl/g. The melting temperature and heat of fusion, as determined by differential scanning calorimetry, were 181.7° C. and 40.3 J/g, respectively.

EXAMPLE 11

Physical Breaking Strength Properties and Data of Representative Fibers Made From Copolymers in Examples 5 through 10

Prior to extruding polymers were dried under vacuum at 40° C. for over 8 hours followed by 80° C. for at least 4 hours. The copolymers were extruded using a ½" single screw extruder. Zone 1 temperature ranged from 125° C. to 175° C. Zone 2 temperature ranged from 175° C. to 230° C. Zone 3 temperature ranged from 195° C. to 230° C. Die temperature ranged from 200° C. to 230° C. Temperatures were dependent on polymer copolymer viscosity. The extrudates were then oriented by drawing 4X to 12X in 2 stages using temperatures of 45° C. to 90° C. and 53° C. to 105° C. for the first and second stages respectively. Thermal and/or tensile properties of representative undrawn and/or drawn fibers are summarized in Table I. Selected drawn monofilaments of copolymers in Examples 5 through 10 were incubated at 37° C. in a phosphate buffer solution at pH of 7.4. The percent strength retention data are included in Table I.

TABLE I

Properties of Representative Fibers

| Example | $T_c$ (°C.) | $T_m$ (°C.) | $\Delta H_f$ (J/g) | Tensile Strength (kpsi) | Modulus (kpsi) | Elongation (%) | % BSR at week 6 | % BSR at week 12 |
|---|---|---|---|---|---|---|---|---|
| 5 | 87.8 | 172.2 | 47 | 90.2 | 683 | 53 | 44 | 40 |
| 6 | 113.6 | 165.9 | 33.8 | 80 | 525 | 59 | — | — |
| 7 | 111 | 164.6 | 30.9 | 84 | 574 | 47 | 62 | — |
| 9 | 118.4 | 169.2 | 28.6 | 106.3 | 647 | 41 | — | — |
| 10 | 103.8 | 167.8 | 26.4 | 96.2 | 726.5 | 37.3 | — | — |

EXAMPLE 12

Preparation of 20/80 Poly-ε-Caprolactone/(95/5 l-Lactide/Trimethylene Carbonate) Segmented Copolymer The reaction apparatus was comprised of a 250 ml round glass boiling flask equipped with a three-way Claisen type adapter, an overhead mechanical stirring unit, and a 90° connector for a vacuum/argon connection. An initial charge of 16.8 grams (0.14672 moles) of poly-ε-caprolactone prepared as described in Example 3, 3.0 grams (0.02934 moles) of trimethylene carbonate, and 80.3 grams (0.55754 moles) of l-lactide was added to the kettle.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature of the oil bath was increased to 140° C. and stirring initiated at 45 rpm. Stirring was stopped after approximately 5 hours. The reaction was maintained at 140° C. for 72 hours.

The inherent viscosity using chloroform as a solvent was 1.13 dl/g. The melting temperature and heat of fusion, as determined by differential scanning calorimetry, were 172.6° C. and 58.6 J/g, respectively.

EXAMPLE 13

Preparation of 92/8 L-Lactide/Trimethylene Carbonate Polymer

The reaction apparatus was comprised of a 1L stainless steel kettle with a 3-neck glass lid equipped with an overhead mechanical stirring unit, vacuum adapter, and a 90° connector for an argon inlet. After obtaining a vacuum of 0.5 mmHg, the apparatus was flame dried. An initial charge of 29.3 grams (0.2844 moles) of trimethylene carbonate, and 471 grams (3.2706 moles) of l-lactide was added to the kettle.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature of the oil bath was increased to 110° C. and stirring initiated at 120 rpm. Upon complete melting and mixing of the contents after approximately one hour, 0.452 milliliters ($2.37 \times 10^{-3}$ moles) of decyl alcohol and 0.889 milliliters ($1.7775 \times 10^{-4}$ moles) of a 0.2M solution of stannous octoate catalyst in toluene were added to the kettle while stirring. The temperature was then increased to 140° C. and stir rate was lowered to approximately 40 rpm. Stirring was stopped after approximately 45 minutes. The reaction was maintained at 140° C. for 48 hours.

The inherent viscosity using chloroform as a solvent was 3.53 dl/g. The melting temperature and heat of fusion, as determined by differential scanning calorimetry, were 182.7° C. and 59 J/g, respectively.

EXAMPLE 14

Preparation of Poly-Trimethylene Carbonate Initiated By 1,3-Propanediol

The reaction apparatus was comprised of a 1-neck 250 ml boiling flask equipped with a 90° connector and a magnetic stir bar. The apparatus was flame dried under nitrogen. An initial charge of 350 grams (3.431 moles) of trimethylene carbonate, 1.738 g ($2.287 \times 10^{-2}$ moles) 1,3-propanediol, and 1.7155 milliliters ($1.7155 \times 10^{-3}$ moles) of a 0.1M solution of stannous octoate catalyst in toluene was added to the flask.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature was then increased to 150° C. Reaction was maintained at 150° C. until the monomer conversion was complete. This was verified by GPC using Dichloromethane as a solvent.

EXAMPLE 15

Preparation of 8/92 Trimethylene Carbonate/(96/4 l-Lactide/Trimethylene Carbonate) Segmented Copolymer The reaction apparatus was comprised of a 1L stainless steel kettle with a 3-neck glass lid equipped with an overhead mechanical stirring unit, vacuum adapter, and two 90° C. for an argon inlet. After obtaining a vacuum of 0.35 mm Hg, the apparatus was flame dried. An initial charge of 58.7 grams (0.575 moles) of poly-trimethylene carbonate from Example 14, 27.0 grams (0.265 moles) of trimethylene carbonate, and 914.3 grams (6.349 moles) of l-lactide was added to the kettle.

The apparatus and its contents were placed under room temperature vacuum for 30 minutes. Using a high temperature oil bath, the apparatus and its contents were heated to 40° C. and kept under vacuum for 30 minutes. The system was then purged with argon. The temperature of the oil bath was increased to 140° C. and stirring initiated at 120 rpm. Upon complete melting and mixing of the contents after 25 minutes, the temperature was decreased to 110° C. After 30 minutes, the temperature was then increased to 140° C. and stir rate was lowered to approximately 40 rpm. Stirring was stopped after approximately 1 hour. The reaction was maintained at 140° C. for 60 hours. At the conclusion of the reaction, the polymer was isolated, ground, and characterized as described for the copolymer of Example 10.

EXAMPLE 16

Preparation of 8/92 Trimethylene Carbonate/(98/2 l-Lactide/Trimethylene Carbonate) Segmented Copolymer The reaction apparatus was comprised of a 1L stainless steel kettle with a 3-neck glass lid equipped with an overhead mechanical stirring unit, vacuum adapter, and two 90° C. for an argon inlet. After obtaining a vacuum of 0.35 mm Hg, the apparatus was flame dried. An initial charge of 58.7 grams (0.575 moles) of poly-trimethylene carbonate from Example 14, 13.5 grams (0.1325 moles) of trimethylene carbonate, and 933.3 grams (6.4813 moles) of l-lactide was added to the kettle.

The copolymerization polymer isolation, and characterization was conducted as in Example 15.

EXAMPLE 17

Preparation of 95/5 $\epsilon$-Caprolactone/glycolide Copolymer Initiated with Malic Acid A mixture of $\epsilon$-caprolactone (136.98 g, 1.2016 mole), glycolide (7.32 g, 0.0631 mole), L-malic acid (16.1 g, 0.12 mole), and stannous octoate (0.632 ml of 0.2 M solution toluene, $1.264 \times 10^{-4}$ mole), was charged into a predried glass reactor equipped for mechanical stirring and providing a dry nitrogen environment. The polymerization mixture was charged and heated at 40° C. under reduced pressure for about 15 minutes and then purged with dry nitrogen. The polymerization was achieved by heating the reactants to 150° C. for 4 hours. The resulting polymer was cooled, isolated, and characterized for identity by NMR and IR, molecular dimension by GPC, and thermal properties by DSC. Key analytical data can be summarized as follows:

$T_m = 46°$ C. $\Delta H_f = 54$ J/g $M_w$(GPC in DCM)=5.95 kiloDaltons

EXAMPLE 18

Preparation of 95/5 $\epsilon$-Caprolactone/glycolide Copolymer Initiated with Malic Acid This copolymer was made to have a higher molecular weight than that of Example 17. Therefore, with the exception of using a smaller amount of malic acid (13.045 g, 0.0974 mole) all other polymerization charge and conditions are similar to those described in Example 17. Key analytical data can be summarized as follows:

$T_m = 45°$ C. $\Delta H_f = 67$ J/g $M_w$(GPC in DCM)=7.10 kiloDaltons

EXAMPLE 19

Preparation of 95/5 $\epsilon$-Caprolactone/glycolide Copolymer Initiated with Malic Acid This copolymer was made to have a much higher molecular weight than that of Example 17. Therefore, with the exception of using a much smaller amount of L-malic acid (11.306 g, 0.084 mole), all other polymerization charges and conditions are similar to those described in Example 17. Key analytical data can be summarized as follows:

$T_m = 47°$ C. $\Delta H_f = 65$ J/g $M_w$(GPC in DCM)=7.72 kiloDaltons

EXAMPLES 20–22

Preparation of 95/5 $\epsilon$-Caprolactone/glycolide Copolymers Initiated with Triethanolamine Following polymerization conditions similar to those used in Example 17, three polymers were made using different amounts of triethanolamine as in Examples 19, 20, and 21. The amounts of monomers, triethanolamine and stannous octoate used are summarized in Table II. Analytical data of the resulting copolymers are also provided in Table II.

Table II

Examples 21–23—Polymerization Charge and Analytical Data of Resulting Copolymers

| | Example 4 | Example 5 | Example 6 |
|---|---|---|---|
| Polymerization Charge | | | |
| Caprolactone | ← 142.4 g, 1.249 mole → | | |
| Glycolide | ← 7.6 g, $6.57 \times 10^{-2}$ mole → | | |
| Triethanolamine | 6.54 g ($4.3 \times 10^{-2}$ mole) | 7.8 g ($5.2 \times 10^{-2}$ mole) | 4.9 g ($3.29 \times 10^{-2}$ mole) |
| Stannous Octoate as 0.2 M solution in toluene | ← 0.655 ml ($1.31 \times 10^{-4}$ mole) → | | |
| Analytical Data | | | |
| $M_W$ (GPC), kDa | 10.80 | 9.05 | 14.30 |
| $T_m$, ° C. | 41 | 41 | 48 |
| $\Delta H_f$, J/g | 66 | 56 | 69 |

EXAMPLE 23

Spinning Multifilament Yarn Using Copolymers of Examples 5–7 and 9, 10, 12, 16–18—General Method The dried, ground polymer is spun using a ¾" single screw extruder equipped for (1) multifilament spinning of 25, 35, 45, 52, and 55 filament yarn; and (2) Godey assembly for spin-drawing or redrawing the spun-drawn yarn. Depending on the polymer molecular weight, the maximum temperature of the polymer melt varies from 205 to 240° C. Single or two-stage drawing is achieved at a temperature range of 60 to 110° C.

EXAMPLE 24

Preparation of Braided Constructs—General Method

Respooled yarn from Example 23 is braided into the desired size using an August Herzog (West-End, N.C.) braider model 80-2/16. Depending on the braid size and intended use, the braid may comprise a core and a sheath or just sheath.

EXAMPLE 25

Preparation of Knitted Constructs—General Method

Different types of knitted fabric having a density of 0.01 to 1 mg/cm$^2$ are constructed from multifilaments of Example 23, using a Lawson Hemphill BAK Knitter (Spartanburg, S.C.).

EXAMPLE 26

Coating Textile Constructs with Acid-Terminated Copolyesters of Examples 17 to 19—General Method A solution of the copolymer and lysine (or arginine) is made in acetone (or other volatile organic solvent) at a concentration of 5 to 20 percent depending on the desired add-on. Depending on the construct geometry, the coating solution is applied by dipping, spraying or continuous metering onto the article. The coated construct is air dried and then dried under reduced pressure to remove residual solvent.

EXAMPLE 27

Coating Textile Constructs with Nitrogenous Copolyesters of Examples 20 to 22—General Method The protocol of Example 26 is used with the exception of substituting the copolyester and amino acid by a nitrogenous copolyester of Examples 20 to 22.

EXAMPLE 28

Coated Braids

Representative examples of the coated braids of Example 26 were tested for their initial strength and their percent retention of their strength after incubation in a phosphate buffer at pH 7.4 and 37° C. The linear breaking strengths of the sutures are summarized in Table III.

TABLE III

Initial Strength and In Vitro Strength Data of Typical Coated Braids

| Suture No. | Source of Polymer | Suture Diameter, mm | Initial Maximum Load, N | % Breaking Strength Retention at | |
|---|---|---|---|---|---|
| | | | | 6 Weeks | 12 Weeks |
| S-I | Example 17 | 0.61 | 97 | 90 | 82 |
| S-II | Example 18 | 0.60 | 93 | 88 | 80 |
| S-III | Example 7 | 0.58 | 95 | 78 | 71 |
| S-IV | Example 12 | 0.52 | 92 | 87 | 78 |

$^a$Composition of copolymers used in preparing the braid:
CL—Caprolactone; TMC = trimethylene carbonate; L = lactide.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicants hereby disclose all sub-ranges of all ranges disclosed herein. These sub-ranges are also useful in carrying out the present invention.

What is claimed is:

1. A bioabsorbable textile construct comprising:
   a preliminary article comprising a crystalline copolymer, comprising
      a copolymer of l-lactide and at least one cyclic monomer, said cyclic monomer comprising a liquid at or above about 40° C.,
      wherein the l-lactide derived sequences of the polymer chain are crystallizable segments or blocks and comprise from about 60 to about 99 percent of all sequences, and
      wherein the copolymer has a $T_m$ of at least 150° C., exhibits a crystallinity of at least about 20%, and has an inherent viscosity of at least about 1.0 dl/g; and
   a coating comprising a nitrogenous copolyester having a molecular weight of less than 20,000 Da and comprising chain sequences covalently linked to a central nitrogen of a tertiary amine, the chain sequences comprising from about 90 to about 98 percent by mole of caprolactone-based units and from about 2 to about 10 percent by mole of glycolide-based units.

2. The bioabsorbable textile construct of claim 1 wherein the preliminary article comprises a suture.

3. The bioabsorbable textile construct of claim 1 wherein the preliminary article comprises a surgical device for use as a tissue-engineered hernial repair patch.

4. The bioabsorbable textile construct of claim 1 wherein the preliminary article comprises a surgical device for use as a tendon, ligament or vascular graft.

5. A bioabsorbable textile construct comprising:
   a preliminary article comprising a crystalline copolymer, comprising
      a copolymer of l-lactide and at least one cyclic monomer, said cyclic monomer comprising a liquid at or above about 40° C.,
      wherein the l-lactide derived sequences of the polymer chain are crystallizable segments or blocks and comprise from about 60 to about 99 percent of all sequences, and wherein the copolymer has a $T_m$ of at least 150° C., exhibits a crystallinity of at least about 20%, and has an inherent viscosity of at least about 1.0 dl/g; and a coating comprising a nitrogenous copolyester having a molecular weight of less than 20,000 Da and comprising chain sequences comprising a major portion of units derived from cyclic monomers and a minor portion of units derived from an acid initiator, the cyclic monomer-based units comprising from about 90 to about 98 percent by mole of caprolactone-based units and from about 2 to about 10 percent by mole of glycolide-based units, wherein the acid-based units are bound to a basic amino acid.

6. The bioabsorbable textile construct of claim 5 wherein the preliminary article comprises a suture.

7. The bioabsorbable textile construct of claim 5 wherein the preliminary article comprises a surgical device for use as a tissue-engineered hernial repair patch.

8. The bioabsorbable textile construct of claim 5 wherein the preliminary article comprises a surgical device for use as a tendon, ligament or vascular graft.

* * * * *